United States Patent
Cardno et al.

(10) Patent No.: US 8,389,236 B2
(45) Date of Patent: Mar. 5, 2013

(54) ASSAY

(75) Inventors: Tony Stuart Cardno, Dunedin (NZ); Warren Perry Tate, Dunedin (NZ)

(73) Assignee: Otago Innovation Limited, Dunedin (NZ)

( * ) Notice: Subject to any disclaimer, the term of this patent is extended or adjusted under 35 U.S.C. 154(b) by 1092 days.

(21) Appl. No.: 12/065,258

(22) PCT Filed: Aug. 30, 2006

(86) PCT No.: PCT/NZ2006/000222
§ 371 (c)(1), (2), (4) Date: Dec. 9, 2008

(87) PCT Pub. No.: WO2007/027106
PCT Pub. Date: Mar. 8, 2007

(65) Prior Publication Data
US 2009/0215051 A1    Aug. 27, 2009

(30) Foreign Application Priority Data

Aug. 30, 2005 (NZ) ........................................ 542111

(51) Int. Cl.
| C12P 21/06 | (2006.01) |
| C12N 15/74 | (2006.01) |
| C12N 5/02 | (2006.01) |
| C12N 15/63 | (2006.01) |

(52) U.S. Cl. ..................... 435/69.1; 435/320.1; 435/325
(58) Field of Classification Search ........................ None
See application file for complete search history.

(56) References Cited

U.S. PATENT DOCUMENTS
6,143,502 A    11/2000    Grentzmann et al.
2003/0049666 A1 *  3/2003   Howard et al. ................... 435/6

FOREIGN PATENT DOCUMENTS
WO    WO 02/077245    10/2002
WO    WO/2004/035628    * 4/2004

OTHER PUBLICATIONS

Score Report for SEQ ID No. 1 search result dated Sep. 15, 2011.*
Arai et al. (2001) "Design of the Linkers Which Effectively Separate Domains of a Bifunctional Fusion Protein," *Protein Eng.* 14(8):529-532.
Bevis et al. (Jan. 2002) "Rapidly Maturing Variants of the *Discosoma* Red Fluorescent Protein (DsRed)," *Nat. Biotechnol.* 20:83-87.
Boulant S et al. (Nov. 14, 2003) "Unusual Multiple Recoding Events Leading to Alternative Forms of Hepatitis C Virus Protein from Genotype 1b," *J. Biol. Chem.* 278(46):45785-45792.
Cariello et al. (1998) "A Novel Bacterial Reversion and Forward Mutation Assay Based on Green Fluorescent Protein," *Mutation Research* 95-105.
Farabaugh et al. (Dec. 1996) "Programmed Translational Frameshifting," *Ann. Rev. Genet.* 30:507-528.
Felgner, J et al. (1993) "Cationic Lipid-Mediated Transfection in Mammalian Cells: 'Lipofection'," *J. Tiss. Cult. Meth.* 15:63-68.
Grentzmann G et al. (1998) "A Dual-Luciferase Reporter System for Studying Recoding Signals," *RNA* 4(4):479-486.
Harger J.W. et al. (2003), An in vivo Dual-Luciferase Assay System for Studying Translational Recoding in the Yeast *Saccharomyces cerevisiae*, *RNA* 9(8):1019-1024.
Hayashi et al. (Jan. 1996) "Orithine Decarboxylase Antizyme: A Novel Type of Regulatory Protein," *Trends Biochem. Sci.* 21(1):27-30.
International Preliminary Report on Patentability for International Application No. PCT/NZ2006/000222, Mailed Jul. 9, 2007.
International Search Report and Written Opinion for International Application No. PCT/NZ2006/000222, Mailed Nov. 23, 2006.
Kollmus H et al. (1996) "Analysis of Eukaryotic mRNA Structures Directing Cotranslational Incorporation of Selenocysteine," *Nucleic Acids Res.* 24(7):1195-1201.
Marqusee et al. (Dec. 1987) "Helix Stabilization by Glu •••Lys$^+$ Salt Bridges in Short Peptides of de novo Design," *Proc. Nat. Acad. Sci. USA* 84:8898-8902
Parkin et al. (Aug. 1992) "Human Immunodeficiency Virus Type 1 *gag-pol* Frameshifting Is Dependant on Downstream mRNA Secondary Structure: Demonstration by Expression in Vivo," *J. Virol.* 66(8):5147-5151.
Prescot et al. (Sep. 10, 1999) "The Length of Polypeptide Linker Affects the Stability of Green Fluorescent Protein Fusion Proteins," *Anal. Biochem.* 273(2):305-307.
Supplementary European Search Report, Corresponding to European Application No. EP 06 79 9576, Completed Jan. 14, 2009.
Tsien R (Jul. 1998) "The Green Fluorescent Protein," *Ann. Rev. Biochem.* 67:509-544.
Yoshinaka et al. (Mar. 1985) "Murine Leukemia Virus Protease is Encoded by the *gag-pol* Gene and is Synthesized Through Suppression of an Amber Termination Codon," *Proc. Nat. Acad. Sci. USA* 82:1618-1622.
Zhang et al. (1999) "A Simple Statistical Parameter for Use in Evaluation and Validation of High Throughput Screening Assays," *J. Biomol. Screen.* 4(2):67-73.

*Primary Examiner* — Nancy T Vogel
*Assistant Examiner* — Catherine Hibbert
(74) *Attorney, Agent, or Firm* — Lathrop & Gage LLP (57) ABSTRACT

The invention relates to a translational recoding reporter construct comprising: a first fluorescent protein coding sequence; a second fluorescent protein coding sequence encoding a fluorescent protein different from the first fluorescent protein; and a linker sequence interposed between the first and second fluorescent protein coding sequence; wherein the first fluorescent protein coding sequence and the second fluorescent protein coding sequence are out-of-frame with respect to each other but are co-expressed as a single fusion polypeptide upon recoding. The invention also relates to methods of use of the construct in screening modulators of recoding.

6 Claims, 2 Drawing Sheets

ASSAY

CROSS-REFERENCE TO RELATED APPLICATIONS

This application is a United States national stage application under 35 U.S.C. §371 of International Application No. PCT/NZ2006/000222, filed Aug. 31, 2006, which claims benefit of New Zealand Patent Application No. 542111 filed Aug. 30, 2005; both of which are hereby incorporated by reference in their entireties to the extent not inconsistent with the disclosure herein.

TECHNICAL FIELD

The present invention is in the field of bioassays, and relates to dual-reporter recoding constructs and methods. Such constructs and methods are useful for screening for drugs that act via modulating recoding.

BACKGROUND ART

There are instances where a single messenger RNA (mRNA) is translated into more than one protein through a process known as "recoding." "Recoding" is a phenomenon where the rules for translation decoding are temporarily altered through specific sites and signals built into the mRNA sequences. In some cases of recoding, special signals are far distant 3' on the message but in most known cases of recoding, the signals are close to the recoding site. In mammalian cells, three kinds of recoding have been described.

First, redefinition of stop codons to sense codons allows synthesis of selenocysteine-containing proteins and synthesis of elongated proteins in many RNA viruses, such as Moloney murine leukemia virus (Yoshinaka et al., 1985, PNAS, 82, 1618-22)

Second, +1 frameshifting regulates expression of ornithine decarboxylase antizyme. The system is autoregulatory and depends on the concentration of polyamines (Hayashi et al., 1996, Trends Biochem Sci, 27-30).

Third, −1 frameshifting is used to synthesize the GagPol precursor polyprotein in retroviruses that have gag (pro), and pol genes in different reading frames. Examples include the human immunodeficiency virus type 1 (HIV-1) gag-pol frameshift (Parkin et al., 1992, J. Virol. 66, 5147-5151).

To aid the study of the elements in messenger RNAs that signal recoding, several reporter systems have been developed. In some systems, recoding is assessed by analysis of .sup.35 S-met-labelled translation products separated by electrophoresis on SDS polyacrylamide gels. Several enzymatic reporter assays have been developed for in vivo studies using chloramphenicol acetyl transferase (cat) or firefly luciferase. Most previous frameshift assays have used dual luciferase reporters used either in vitro, or in vivo in either yeast or bacterial cells. Although luciferase provides good sensitivity, such systems suffer from the disadvantage of the requirement for expensive buffers.

The use of fluorescent proteins, such as Green Fluorescent Proteins (GFPs), as reporters provide a potential advantage in that no expensive buffers are required and further that time savings are possible due to quicker assay set up and read times. However, a significant disadvantage of use fluorescent proteins as reporters, is that there is typically no amplification of the output signal and as a result, sensitivity is lower than with enzyme based reporters such as luciferase.

Fluorescent proteins have been used in assays in bacterial cells but as far as the applicants are aware, no dual reporter frameshift constructs or assays, using fluorescent proteins as reporters, have been developed for successful use in mammalian cells.

Recoding assays have application in drug screening to identify compounds useful for treatment of disorders in humans involving organisms which rely on such frameshift systems in their life cycles. Thus it would be beneficial to perform such assays in mammalian cells as opposed to yeast or bacterial cells.

The human ribosome slips backwards when decoding the HIV-1 RNA, thereby shifting its three letter reading-frame, and this occurs about 5-10% of the time it encounters the slippage site. This ratio is essential for the viability of the virus, ensuring not only the correct ratio of its structural and enzyme proteins, but also ensuring correct assembly of the viral particles. The slippage is an example of −1 frameshifting. Two elements, a slippery heptamer sequence, U UUU UUA, and an adjacent secondary structural element in the HIV-1 RNA, are critical. An assay that measures how test compounds affect the efficiency of the frameshifting is of value to exploit this as a potential antiviral target.

It is an object of the invention to provide a fluorescent protein-based translational recoding reporter construct and assay which may be used in mammalian cells.

SUMMARY OF THE INVENTION

In the first aspect, the invention provides a translational recoding reporter construct comprising
a) a first fluorescent protein coding sequence;
b) a second fluorescent protein coding sequence encoding a fluorescent protein different from the first fluorescent protein; and
c) a linker sequence interposed between the first and second fluorescent protein coding sequence;
wherein the a first fluorescent protein coding sequence and the second fluorescent protein coding sequence are out-of-frame with respect to each other but are co-expressed as a single fusion polypeptide upon recoding.

In a preferred embodiment the linker sequence encodes a polypeptide capable of physically separating the co-expressed fluorescent proteins, resulting in increased fluorescence output from each protein. Preferably the encoded linker reduces fluorescence resonance energy transfer (FRET) between the co-expressed fluorescent proteins.

Preferably the linker encodes a polypeptide comprising a sequence between 2 and 100, more preferably between 3 and 75, more preferably between 4 and 60, more preferably between 7 and 52 and most preferably between 10 and 20 amino acids in length.

Preferably the linker encodes a polypeptide comprising the motif A(EAAAK)$_n$A wherein n is a number between 1 and 10. More preferably n=2. Most preferably the linker encodes the sequence of SEQ ID NO: 1. The linker may include additional nucleotides to facilitate cloning. Preferably the linker comprises the sequence of SEQ ID NO:2.

In a further embodiment fluorescent proteins are a red fluorescent protein and a green fluorescent protein. Preferably the red fluorescent protein encoding sequence is downstream of the green fluorescent protein encoding sequence. Suitable red fluorescent proteins include DsRed that is commercially available from Clontech.

Suitable green fluorescent proteins include Enhanced green fluorescent protein that is commercially also available from Clontech.

In a further embodiment the reporter construct comprises a recoding signal sequence interposed between the first fluorescent protein coding sequence and the second fluorescent protein coding sequence.

Preferably the recoding signal sequence is a frameshift signal sequence.

Preferably the frameshift signal sequence is interposed between the first fluorescent protein coding sequence and the linker sequence.

Preferably the frameshift signal sequence signal is a −1 frameshift signal sequence.

Preferably the −1 frameshift signal sequence signal is an HIV-1 gag/pol frameshift signal sequence Preferably the frame shift signal sequence comprises the sequence of SEQ ID NO:8.

In a further aspect the invention provides a vector comprising the translational recoding reporter construct of the invention.

In a further aspect the invention provides a host cell comprising a translational recoding reporter construct of the invention.

In a further aspect the invention provides a host cell comprising a vector of the invention.

The host cell may be either transiently or stably transformed with a construct of the invention.

In a preferred embodiment the host cell is stably transformed with a construct of the invention.

In a further aspect the invention provides a method of assaying conditions which modulate translational recoding comprising the steps:
a) providing a translational recoding reporter construct of the invention including a recoding sequence;
b) under test conditions
  i) transcribing the construct to produce a transcript corresponding to the first and second fluorescent proteins;
  ii) translating the transcript from i) to produce the first fluorescent protein, and a fusion protein comprising the first and second fluorescent proteins;
  iii) measuring a fluorescence signal from of each of the fluorescent proteins and produced in ii);
c) under control conditions
  i) transcribing the construct to produce a transcript corresponding to the first and second fluorescent proteins;
  ii) translating the transcript from i) to produce first fluorescent protein and a fusion protein comprising the first and second fluorescent proteins;
  iii) measuring a fluorescence signal from each of the fluorescent proteins and produced in ii);
d) comparing the ratio of fluorescence signal from each of the fluorescent proteins in b) with the ratio of fluorescence signal from each of the fluorescent proteins in c) wherein a difference in the ratio indicates that the test conditions modulate recoding In a preferred embodiment of the method, under the test conditions, a test composition is contacted with the construct of the invention in order to assess whether the composition modulates recoding. Under the corresponding control conditions, the test composition is not contacted with the construct of the invention. Under control conditions, the test composition may be replaced by a suitable control composition.

In a further aspect the invention provides a method of assaying conditions which modulate translational recoding in vivo comprising the steps:
a) providing host cells comprising a translational recoding reporter construct of the invention including a recoding sequence;
b) incubating at least one host cell under test conditions
  i) transcribing the construct to produce a transcript corresponding to the first and second fluorescent proteins;
  ii) translating the transcript from i) to produce the first fluorescent protein, and a fusion protein comprising the first and second fluorescent proteins;
  iii) measuring a fluorescence signal from of each of the fluorescent proteins;
c) incubating at least one host cell under control conditions
  i) transcribing the construct to produce a transcript corresponding to the first and second fluorescent proteins;
  ii) translating the transcript from i) to produce the first fluorescent protein, and a fusion protein comprising first and second fluorescent proteins;
  iii) measuring a fluorescence signal from each of the fluorescent proteins;
d) comparing the ratio of fluorescence signal from each of the fluorescent proteins in b) with the ratio of fluorescence signal from each of the fluorescent proteins in c) wherein a difference in the ratio indicates that the test conditions modulate recoding.

In a preferred embodiment of the method, under the test conditions, a test composition is contacted with the host cell comprising the construct of the invention in order to assess whether the composition modulates recoding. Under the corresponding control conditions, the test composition is not contacted with the construct of the invention. Under control conditions, the test composition may be replaced by a suitable control composition.

In a further aspect the invention provides a method for identifying a modulator of recoding, the method comprising the steps:
a) providing host cells comprising a translational recoding reporter construct of the invention including a recoding signal;
b) incubating at least one host cell in the presence of a compound to be screened
  i) transcribing the construct to produce a transcript corresponding to the first and second fluorescent proteins;
  ii) translating the transcript from i) to produce the first fluorescent protein, and a fusion protein comprising the first and second fluorescent proteins;
  iii) measuring a fluorescence signal from of each of the fluorescent proteins;
c) incubating at least one host cell under control conditions
  i) transcribing the construct to produce a transcript corresponding to the first and second fluorescent proteins;
  ii) translating the transcript from i) to produce the first fluorescent protein, and a fusion protein comprising the first and second fluorescent proteins;
  iii) measuring a fluorescence signal from each of the fluorescent proteins;
d) comparing the ratio of fluorescence signal from each of the fluorescent proteins in b) with the ratio of fluorescence signal from each of the fluorescent proteins in c) wherein a change in the ratio indicates that compound is a modulator of recoding In a further aspect the invention provides a modulator of recoding identified by a method of the invention.

The host cells of the invention, or for use in the methods of the invention, may be any type of cell. Preferably the host cells are eukaryotic. More preferably the host cells are mammalian cell. Preferred mammalian cell types include but are not limited to COS-7 cells, Jurkat cells, T lymphocyte cells isolated from human blood, 293T cells and HEK cells.

Particularly Preferred Cells are COS-7.

Also preferred are cells adapted to be transformed by site-directed transformation. Such cells include Flp-In CV1 cells that are commercially available from Invitogen Life Technologies.

In a preferred embodiments the methods additionally include use of a control construct similar to that of the construct of the invention except that in the control construct the first and second fluorescent proteins are configured to be permanently in frame such that the first and second proteins are always co-expressed as a fusion protein, without the need for recoding. In this embodiment of the method both the translational reporter construct of the invention and the control construct are subjected to both test conditions and control conditions. Recoding is then assessed using the formula:

((Second fluorescent protein signal from recoding construct under test conditions/First fluorescent protein signal from recoding construct under test conditions))/((Second fluorescent protein signal from control construct under test conditions/First fluorescent protein signal from control construct under test conditions))*100

DETAILED DESCRIPTION OF THE INVENTION

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or fort part of the common general knowledge in the art.

The term comprising, and grammatical equivalents thereof, is intended to mean "consisting at least in part of . . . ".

The term "polynucleotide(s)", as used herein, means a single or double-stranded deoxyribonucleotide or ribonucleotide polymer, and include as non-limiting examples, coding and non-coding sequences of a gene, sense and antisense sequences, exons, introns, genomic DNA, cDNA, pre-mRNA, mRNA, rRNA, siRNA, miRNA, tRNA, ribozymes, recombinant polynucleotides, isolated and purified naturally occurring DNA or RNA sequences, synthetic RNA and DNA sequences, nucleic acid probes, primers, fragments, genetic constructs, vectors and modified polynucleotides.

The term "primer" refers to a short polynucleotide, usually having a free 3'OH group, that is hybridized to a template and used for priming polymerization of a polynucleotide complementary to the target.

The term "polypeptide", as used herein, encompasses amino acid chains of any length, including full-length proteins, in which amino acid residues are linked by covalent peptide bonds. Polypeptides of the present invention may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "translational recoding reporter construct" refers to a polynucleotide molecule, usually double stranded DNA, typically comprising in a 5' to 3' direction:
1) a promoter;
2) a polynucleotide encoding a first fluorescent protein;
3) a recoding signal sequence;
4) a linker sequence encoding a polypeptide sequence capable of physically separating the expressed fluorescent proteins;
5) a polynucleotide encoding a second fluorescent protein; and
6) optionally a termination signal A "transitional recoding reporter construct" thus contains the necessary elements for transcribing and translating either the first fluorescent protein only, or upon recoding transcribing and translating a fusion protein comprising the first fluorescent protein and the second fluorescent protein separated by the encoded linker polypeptide sequence.

Such a construct may be transcribed and translated in vitro or in vivo. The choice of transcriptional/translational elements will depend on whether in vitro and in vivo transcription and translation is desired.

When the translational reporter construct of the invention is to be transcribed/translated, an in vivo promoter capable of driving expression in the preferred host cell should be chosen. Likewise a terminator functional in the preferred host cell may optionally be included.

It will also be appreciated by those skilled in the art that the specific fluorescent proteins described for use in the recoding construct of the invention can be replaced with other fluorescent protein sequences to provide alternative construct suitable for assessing recoding sequences. Such alternative constructs are also encompassed by the invention. Other fluorescent protein sequences are known in the art, see for example Tsien R (Annu Rev Biochem. 1998; 67:509-44) which is incorporated herein by reference.

It will be appreciated by those skilled in the art that the specific recoding sequence described, for use in the recoding construct of the invention, can also be replaced with other recoding sequences to provide alternative construct suitable for assessing or assaying conditions associated with modulation of other such recoding sequences. Such alternative constructs are also encompassed by the invention. Other recoding sequences are known in the art and are reviewed in Farabaugh et al (Annual Review of Genetic, 1996, Vol 30, 507-528) which is incorporated herein by reference.

Other linker sequences may also be used to provide alternative constructs of the invention suitable for assessing recoding sequences. Such alternative constructs are also encompassed by the invention. Other linker sequences are known in the art, see for example Marqusee and Baldwin (PNAS, 1987, 84, 8898-8902) and Prescot et al (Analytical Biochemistry, 1999, 273, 305-307) which are incorporated herein by reference.

The transcriptional reporter construct may be inserted into, or joined to, a vector.

The term "vector" refers to a polynucleotide molecule, usually double stranded DNA, which is used to transport a construct, such as a translational recoding reporter construct of the invention, into a host cell. The vector may be capable of replication in at least one additional host system, such as E. coli. The vector may also include a sequence to allow for selection of the vector in such an additional host system.

The term "composition" includes individual components, combinations of compounds and extracts from naturally occurring organisms which may be composed of several components.

The Applicants have developed dual fluorescent protein reporter-based constructs and assays useful for assessing conditions which alter recoding. The Applicants discovered that insertion of a linker sequence, of a specific formula, significantly improves the output signal obtainable from the two fluorescent proteins encoded by the construct. This allows the assay to be performed in vivo in host cells comprising a construct of the invention.

The invention provides translational recoding constructs and vectors. Methods for producing assembling constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

The invention also provides host cells comprising the constructs and vectors of the invention. Methods for introducing constructs and vectors into host cells are well-known to those skilled in the art Felgner, J et al (J. Tiss. Cult. Meth. 15:63 (1993)

Host cells may be transiently transformed into with constructs or vectors. Alternatively host cell lines may be developed which are stably transformed with a construct of the invention. Again such methods for transient or stable transformation are well-known to those skilled in the art.

Preferably the host cells of the invention are stably transformed with the construct of the invention. Preferably the host cells of the invention are mammalian cells. Particularly preferred systems for production of stable transformed mammalian cells are those in which the construct may be inserted at a specific site in the host cell genome. This provides the opportunity to minimize any differences in test and control host cells due to differences in insertion sites. One such system is the Flp-In system that is commercially available from Invitrogen Life Technologies.

The invention provides assays for assessing conditions which result in the modulation of recoding.

Such assays can be performed in vitro through application of a suitable in vitro transcription/translation system, paired with use of complementary transcriptional/translational elements in the construct of the invention.

The invention provides methods for assessing conditions which result in the modulation of recoding in vivo. Such assays typically involve use of host cells of the invention comprising constructs of the invention.

Any conditions of interest may be compared in such assays. Particularly preferred conditions are those in which various compounds may be tested for the effect on modulation of recoding.

The invention provides methods of screening for modulators of recoding in vivo. Modulators may be agonists or antagonists. And the methods may be adapted to enhance identification of agonists or antagonists.

The methods of screening may involve high throughput techniques. The methods of the invention are preferably performed in multiwell plates. Preferably plates with at least 24 wells, more preferably at least 48 wells, most preferably at least 96 wells are utilised.

Preferably fluorescence plate readers are employed in the methods of the inventions. Preferably fluorescence intensity is employed when reading the plates.

More preferably fluorescence polarization is employed when reading the plates.

Alternatively flow-cytometric methods may be employed to assess recoding in the methods of the invention.

Potential antagonists and antagonists include but are not limited to small organic molecules, peptides, polypeptides, antibodies and natural extracts from any organism, particularly plants. The screening of compound or peptide libraries in the method of the invention is also contemplated.

BRIEF DESCRIPTION OF THE DRAWINGS

The present invention will be better understood with reference to the accompanying drawing in which.

EXAMPLES

The invention will now be illustrated with reference to the following non-limiting examples.

Example 1

Production of a Recoding Construct of the Invention

Plasmid Backbone

The plasmid pDsRed.T4-N1 was used as a backbone for producing a translational recoding reporter construct. pDsRed.T4-N1 is derived from pDsRed1-N1 (Clontech) but contains 10 codon changes that collectively reduced the aggregation and accelerate the maturation of the encoded DsRed.T4-N1. The vector contains a Kan resistance marker rather than Amp resistance. The vector backbone is unchanged except that the AgeI site immediately upstream of the start codon has been changed to a SpeI site. There are also several changes near the 5' end of the DsRed.T4-N1. gene (Bevis, B and Glick B, Nature Biotechnology, 2002, 20, 83-90).

Insertion of Green Fluorescent Protein

The enhanced green fluorescent protein (EGFP) coding sequence was amplified by PCR from the EGFP-N1 plasmid (Clontech) using primers designed to add a Hind III site at the 5' end, and to remove the stop codon at the 3' end and simultaneously introduce an Eco RI site. The primers used for amplifying EGFP were as follows:

```
EGFP forward primer without linker:
                                       (SEQ ID NO: 4)
GATCCG AAGCTT GCCACC ATG GTGAGCAAGGGCGAGGAGC EGFP reverse primer:
                                       (SEQ ID NO: 5)
GCGGCC GAATTC CTTGTACAGCTCGTCCAT
```

The amplified EGFP sequence was cloned into pDsRed.T4-NI, upstream of DsRedT4-N1, by standard techniques.

Eliminating the ATG Start from DsRed.T4

In order to remove the ATG start codon from DsRed.T4 and to replace the start codon with a Bam HI site, the DsRed.T4 sequence was amplified from the pDsRed.T4.N1 plasmid using the following primers:

```
DsRed.T4 forward primer (contains Bam HI site
GGATGC):
                                       (SEQ ID NO: 6)
GTCGCCACC GGATCC TCC TCC GAG GAC GTC ATC AA DsRed.T4 reverse primer (contains Not I site
GCGGCCGC):
                                       (SEQ ID NO: 7)
CTAGAGTC GCGGCCGC TACAGGAA
```

The DsRed.T4 sequence in pDsRed.T4-N1 sequence was removed and replaced with the modified (no start codon) sequence by standard cloning techniques.

Construction of the Recoding Sequence

Two oligonucleotides were used to make an HIV-1 stem loop/pseudo knot sequence to be inserted as a recoding sequence, between the EGFP and the DsRed genes. The following oligonucleotides were used:

```
HIV forward oligonucleotide with pseudoknot:
                                      (SEQ ID NO: 8)
AATTC GGA CAG GCT AAT TTT TTA GGG AAG ATC TGG CCT

TCC TAC AAG GGA AGG CCA GGG AAT TTT CTT TAA ACG

CCG C

HIV reverse oligonucleotide with pseudoknot
                                      (SEQ ID NO: 9)
GG CGT TTA AAG AAA ATT CCC TGG CCT TCC CTT GTA GGA

AGG CCA GAT CTT CCC TAA AAA ATT AGC CTG TCC G
```

These oligonucleotides were annealed and the resulting double-stranded sequence was cloned between the EcoRI site and the SacII site of the vector, all using standard molecular techniques.

Figure 1:
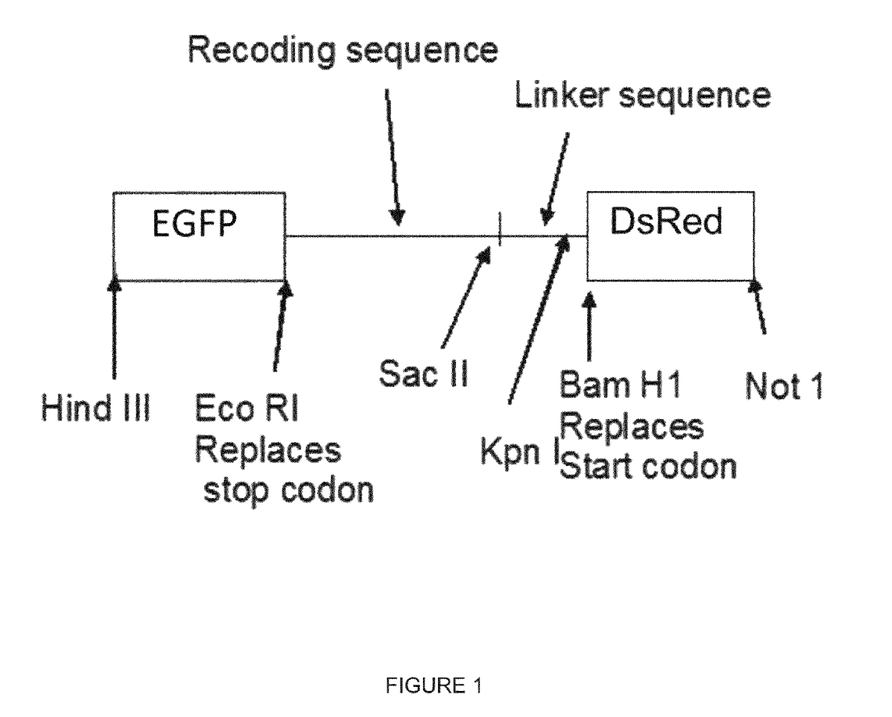
FIG. 1 shows a diagrammatic representation of the recoding construct of the invention.
Figure 2:
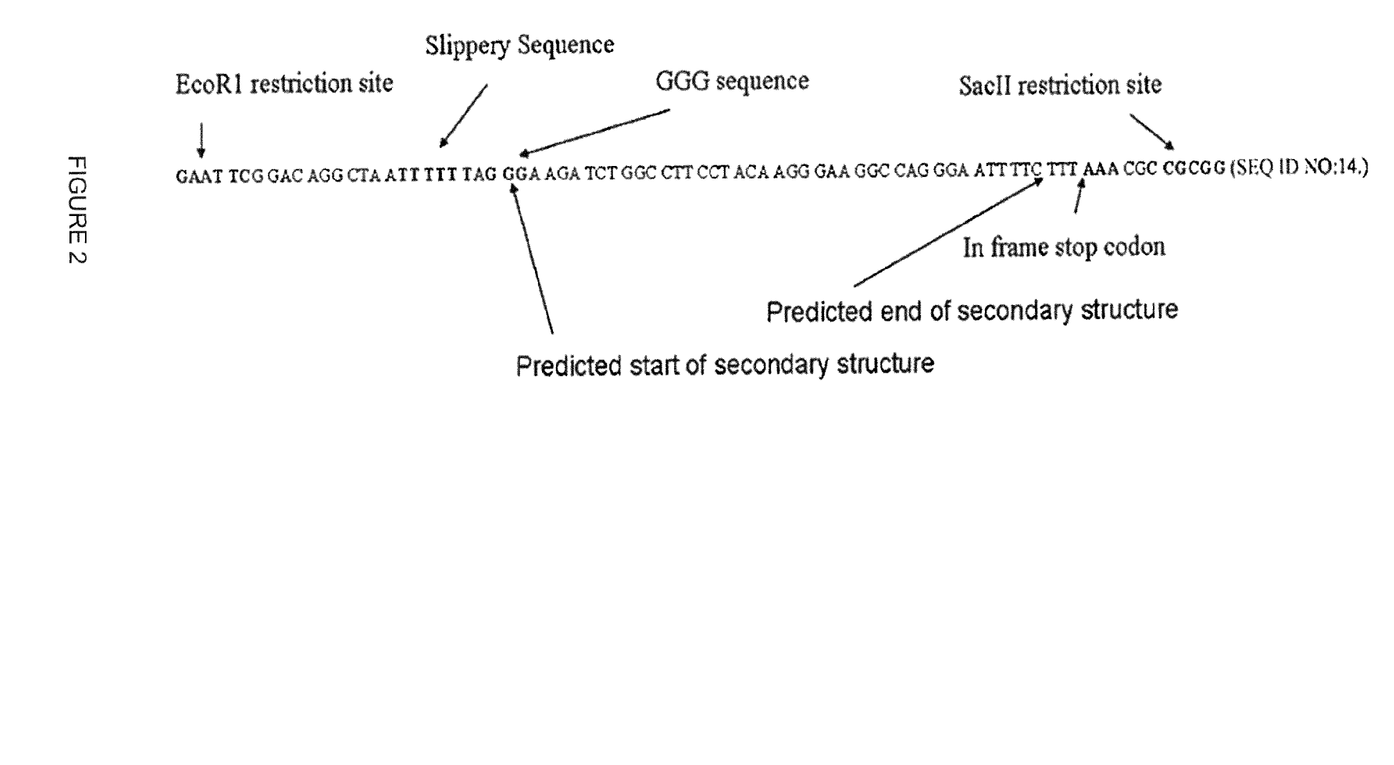
FIG. 2 shows features of a HIV-1 gag pol recoding sequence used in a translational recoding reporter construct of the invention.

Features of the HIV-1 insert are shown in FIG. 1.

The HIV-1 recoding sequence insert was cloned into the translational recoding reporter construct between the 3' end of EGFP-N1 and the 5' end of DsRed.T4-N1 between EcoRI and SacII sites.

Having a SacII site and a BamH1 for the start of the DsRed allowed for linkers or other sequences to be inserted in the future if desired. The in frame stop codon with a strong context (TAA A) is to stop any sequence being translated after the HIV-1 sequence unless it is bypassed by a frameshift event. The stop codon TAAA is followed by two bases CG to have the DsRed reporter in the correct reading frame.

Control Construct

A control construct without a frameshift was also produced—in much the same way as the recoding construct, and termed Null0. In the Null0 construct, slippery sequence was changed so the sequence shouldn't slip on the ribosome and an A was added before the GGG to force a permanent frameshift into the 0 frame.

UUU UUA of the slippery sequence was changed to UUC CUA in the Null0 construct. In both constructs the sequence encodes Phenylalanine, Leucine, so there is no change in the amino acids being incorporated.

Two oligonucleotides were used to make the HIV-1 stem loop/pseudo knot with the Null0 frame sequence to be inserted between the EGFP and the DsRed genes:

```
Null 0 forward:
                                      (SEQ ID NO: 10)
ATT TCG GAC AGG CTA ATT TCC TAA GGG AAG ATC TGG

CCT TCC TAC AAG GGA AGG CCA GGG AAT TTT CCT TAA

ACG CCG C

Null0 reverse:
                                      (SEQ ID NO: 11)
GGC GTT TAA AGA AAA TTC CCT GGC CTT CCC TTG TAG

GAA GGC CAG ATC TTC CCT TAG GAA AAT AGC CTG TCC G
```

These oligonucleotides were annealed and the resulting double-stranded sequence was cloned between the EcoRI site and the SacII site of the vector, all using standard molecular techniques.

Insertion of a Linker Sequence

In order to improve upon the signal strength of the dual GFP system and improve the utility of the recoding construct the applicants postulated that a linker sequence placed between the two fluorescent proteins may be beneficial. The applicants considered that such a linker may spatially separate the fluorescent proteins and potentially reduce fluorescence resonance energy transfer (FRET).

A linker was designed, based on Arai et al (Protein engineering vol 14, no 8, pp 529-532, (2001), with a SacII restriction site at the 5' end and a BamH1 at the 3' end to facilitate cloning. The following oligonucleotides were used to produce the linker insert:

```
Linker forward:
                                      (SEQ ID NO: 12)
GGG CCC GGC CGA AGC AGC CGC AAA AGA AGC AGC CGC

CAA AGC TAC CG

Linker reverse:
                                      (SEQ ID NO: 13)
GAT CCG GTA CCG GCT TTG GCG GCT GCT TCT TTG GCG

GCT TCG GCC GGG CCC GC
```

These oligonucleotides were annealed and the resulting double stranded sequence was cloned with the recoding vector between the SacII site and the BamHI site. An additional KpnI site was placed just 5' to the SacII in the linker sequence to allow for future linkers to be inserted between the KpnI and the BamHI sites.

Example 2

Production of Cell Lines Stably Transformed with a Recoding Construct of the Invention The translational recoding construct described above was excised via Hind III and Not I restrictions sites and ligated into a Flp-In™ pcDNA5/FRT expression vector (Invitrogen Life Technologies) before being stably transformed into Flp-In™ CV1 cells (Invitrogen Life Technologies) according to the manufacturer's instructions.

Example 3

Dual Fluorescent Reporter Recoding Assay using Cycloheximide at 50 nM

Mammalian COS-7 cells were grown, harvested, trypsinised, washed and diluted to $1 \times 10^5$ cells/ml all under standard conditions.

The diluted cells were then split into two equal portions. One portion was transiently transfected with the recoding construct, and other with the Null 0 frame control construct. Transient transfection was performed using 2 μL of FuGENE® 6 transfection reagent (Roche) and 500 ng of DNA for every mL of cells, in accordance with the manufacturing instructions.

Transfected cells were seeded in 24 well plates under standard conditions. Cycloheximide was added in triplicate at 50 nM and the plates were then incubated for 48 hours at 37° C.

The cells were washed 3 times with Phosphate Buffered Saline (PBS) to remove any traces of culture medium. 100 ul of Passive Lysis buffer (Promega) was added. The cells were frozen. The frozen cells were then thawed and transferred to a 96 well plate, and fluorescence intensity was read in the BMG PolarStar plate reader.

Plate reader settings were as follows:
EGFP readings:
Filters 485 excitation, 520-P emission DsRed readings:
Filters 544 excitation, 590 emission
Results:
DsRed Signal at 544 Excitation, 590 Emission
  HIV-1 frameshift construct, relative fluorescent Units (RFU): 1440, 1465, 1436 (average=1447) minus control=1342
  Null 0 frameshift construct, RFU: 42296, 44610, 43883 (average=43596) minus control=43491
  No Drug control HIV-1 frameshift construct RFU: 1633, 1712, 1783 (average=1709) minus control=1604
  No Drug control Null 0 frameshift construct RFU: 47018, 45488, 47645 (average=46717) minus control=46612
  Control cells: 94, 101, 120 average=105
EGFP Signal at 485 Excitation, 520-P Emission
  HIV-1 frameshift construct, RFU: 24081, 25224, 23500 (average=24268) minus control=23858
  Null 0 frameshift construct RFU: 40751, 42960, 42452 (average=42054) minus control=41644
  No Drug control HIV-1 frameshift construct RFU: 26282, 27475, 29790 (average=27849) minus control=27439
  No Drug control Null 0 frameshift construct RFU: 46264, 43852, 46747 (average=45621) minus control=45211
  Control cells: 374, 395, 462 average=410
Frameshift Calculation:
  [[DsRed signal: HIV-1 frameshift construct]/[EGFP signal: HIV-1 frameshift construct]]/[[DsRed signal: Null 0 frameshift construct]/[EGFP signal: Null 0 frameshift construct]]
  Cycloheximide: ((1342/23858))/((43491/41644)) *100=5.38% frameshift
  No drug control: ((1604/27439))/((46612/45211)) *100=5.67% frameshift
  The results show a decrease in frameshift from 5.67% to 5.38% This is an absolute change frameshift efficiency of 0.29% or a decrease by 5% from the original 5.67% and demonstrates the utility of the recoding construct and methods of the invention in detecting recoding changes.

Example 4

Dual Fluorescent Reporter Recoding Assay using Anisomycin at 50 nM

Mammalian COS-7 cells were grown, harvested, trypsinised, washed and diluted to $1 \times 10^5$ cells/ml all under standard conditions.
The diluted cells were then split into two equal portions. One portion was transfected, as described in Example 3, with the recoding construct, and other with the Null 0 frame control construct.
Cells were then seeded in 24 well plates under standard conditions. Anisomycin was added in triplicate at 50 nM and the plates were then incubated for 48 hours at 37° C.
The cells were washed 3 times with Phosphate Buffered Saline (PBS) to remove any traces of culture medium. 100 ul of Passive Lysis buffer (Promega) was added. The cells were frozen. The frozen cells were then thawed and transferred to a 96 well plate, and fluorescence intensity was read in the BMG PolarStar plate reader.
Plate reader settings were as follows:
EGFP readings:
Filters 485 excitation, 520-P emission DsRed readings:
Filters 544 excitation, 590 emission
Results:
DsRed Signal at 544 Excitation, 590 Emission
  HIV-1 frameshift construct, Relative fluorescent Units (RFU): 1999, 1992, 1936 (average=1975) minus control=1891
  Null 0 frameshift construct RFU: 58875, 59005, 57000 (average=58293) minus control=58209
  No Drug control HIV-1 frameshift construct RFU: 1911, 1849, 2110 (average=1956) minus control=1872
  No Drug control Null 0 frameshift construct RFU: 51117, 54577, 52708 (average=52800) minus control=52716
  Control cells: 86, 78, 88 average=84
EGFP Signal at 485 Excitation, 520-P Emission
  HIV-1 frameshift construct RFU: 33622, 31866, 32512 (average=32666) minus control=32336
  Null 0 frameshift construct RFU: 57527, 57165, 54783 (average=56491) minus control=56161
  No Drug control HIV-1 frameshift construct RFU: 29849, 30927, 33416 (average=31397) minus control=31067
  No Drug control Null 0 frameshift construct RFU: 50596, 54274, 52605 (average=52491) minus control=52161
  Control cells: 331, 332, 328 average=330
Frameshift Calculation:
  [[DsRed signal: HIV-1 frameshift construct]/[EGFP signal: HIV-1 frameshift construct]]/[[DsRed signal: Null 0 frameshift construct]/[EGFP signal: Null 0 frameshift construct]]
  Anisomycin: ((1891/32336))/((58209/56161)) *100=5.64% frameshift
  No drug control: ((1872/31067))/((52716/52161)) *100=5.96% frameshift
  A decrease in frameshift from 5.96% to 5.64% This is an absolute change frameshift efficiency of 0.32% or a decrease by 5.3% from the original 5.96% and again demonstrates the utility of the recoding construct and methods of the invention in detecting changes Example 5

Dual Fluorescent Reporter Recoding Assay using a Range of Cycloheximide Concentrations The cells were prepared as described in examples 3 and 4. Cyloheximide was added to cells seeded in a 24 well plate, to give final concentrations of 0 nM (no drug) 100 nM, 200 nM, 300 nM, 400 nM and 500 nM.
Plate reader settings were as follows:
Note the filters are different from examples 3, 4 and give slightly different frameshift efficiencies.
DsRed signal at 525 excitation, 600LP emission
EGFP signal at 485 excitation, 520-P emission
Results are shown in Tables 1 to 5 below.

TABLE 1

Minus 1 Frameshift Construct
DsRed 525 excitation 600LP emission

|   | 100 nM | 200 nM | 300 nM | 400 nM | 500 nM | No Drugs | Controls |
|---|---|---|---|---|---|---|---|
| A | 2103 | 2491 | 2601 | 2623 | 2857 | 2499 | 584 |
| B | 2532 | 2581 | 2855 | 2835 | 2804 | 2388 | 653 |
| C | 2516 | 2629 | 2567 | 2654 | 2709 | 2568 | 637 |
| D |  |  |  |  |  |  |  |
| E |  |  |  |  |  |  |  |
| F |  |  |  |  |  |  |  |
| G |  |  |  |  |  |  |  |
| H |  |  |  |  |  |  |  |
| Average | 2384 | 2567 | 2674 | 2704 | 2790 | 2485 | 625 |
| Standard Deviation | 243 | 70 | 157 | 115 | 75 | 91 | 36 |
| Background | 625 | 625 | 625 | 625 | 625 | 625 |  |
| St Dev Background | 36 | 36 | 36 | 36 | 36 | 36 |  |
| Z, Z' factor | 0.52 | 0.84 | 0.72 | 0.78 | 0.85 | 0.80 |  |

TABLE 2

Null 0 Frameshift Construct
DsRed 525 excitation 600LP emission

|   | 100 nM | 200 nM | 300 nM | 400 nM | 500 nM | No Drugs | Controls |
|---|---|---|---|---|---|---|---|
| A | 39194 | 36501 | 44790 | 41612 | 41554 | 30650 | 584 |
| B | 39297 | 41946 | 48463 | 39009 | 39489 | 39971 | 653 |
| C | 38886 | 42010 | 42252 | 43311 | 42970 | 38002 | 637 |
| D |  |  |  |  |  |  |  |
| E |  |  |  |  |  |  |  |
| F |  |  |  |  |  |  |  |
| G |  |  |  |  |  |  |  |
| H |  |  |  |  |  |  |  |
| Average | 39126 | 40152 | 45168 | 41311 | 41338 | 36208 | 625 |
| Standard Deviation | 214 | 3162 | 3123 | 2167 | 1751 | 4913 | 36 |
| Background | 625 | 625 | 625 | 625 | 625 | 625 |  |
| St Dev Background | 36 | 36 | 36 | 36 | 36 | 36 |  |
| Z, Z' factor | 0.98 | 0.76 | 0.79 | 0.84 | 0.87 | 0.58 |  |

TABLE 3

Minus 1 Frameshift Construct
EGFP 485 excitation 520-P emission

|   | 100 nM | 200 nM | 300 nM | 400 nM | 500 nM | No Drugs | Controls |
|---|---|---|---|---|---|---|---|
| A | 20041 | 24507 | 26093 | 27167 | 28882 | 23535 | 565 |
| B | 24670 | 26349 | 29013 | 28670 | 29092 | 22910 | 595 |
| C | 24494 | 26524 | 26485 | 27003 | 27871 | 23623 | 592 |
| D |  |  |  |  |  |  |  |
| E |  |  |  |  |  |  |  |
| F |  |  |  |  |  |  |  |
| G |  |  |  |  |  |  |  |
| H |  |  |  |  |  |  |  |
| Average | 23068 | 25793 | 27197 | 27613 | 28615 | 23356 | 584 |
| Standard Deviation | 2623 | 1117 | 1585 | 919 | 653 | 389 | 17 |
| Background | 584 | 584 | 584 | 584 | 584 | 584 |  |
| St Dev Background | 17 | 17 | 17 | 17 | 17 | 17 |  |
| Z, Z' factor | 0.65 | 0.87 | 0.82 | 0.90 | 0.93 | 0.95 |  |

TABLE 4

Null 0 Frameshift Construct
EGFP 485 excitation 520-P emission

|   | 100 nM | 200 nM | 300 nM | 400 nM | 500 nM | No Drugs | Controls |
|---|---|---|---|---|---|---|---|
| A | 41092 | 38594 | 46002 | 42952 | 42851 | 31724 | 565 |
| B | 41270 | 43997 | 50057 | 41038 | 40790 | 41716 | 595 |
| C | 41182 | 43770 | 43726 | 44861 | 44585 | 39104 | 592 |
| D |  |  |  |  |  |  |  |
| E |  |  |  |  |  |  |  |

TABLE 4-continued

Null 0 Frameshift Construct
EGFP 485 excitation 520-P emission

|  | 100 nM | 200 nM | 300 nM | 400 nM | 500 nM | No Drugs | Controls |
|---|---|---|---|---|---|---|---|
| F |  |  |  |  |  |  |  |
| G |  |  |  |  |  |  |  |
| H |  |  |  |  |  |  |  |
| Average | 41181 | 42120 | 46595 | 42950 | 42742 | 37515 | 584 |
| Standard Deviation | 89 | 3056 | 3207 | 1912 | 1900 | 5182 | 17 |
| Background | 584 | 584 | 584 | 584 | 584 | 584 |  |
| St Dev Background | 17 | 17 | 17 | 17 | 17 | 17 |  |
| Z, Z' factor | 0.99 | 0.78 | 0.79 | 0.86 | 0.86 | 0.58 |  |

TABLE 5

| Cycloheximide Titration | 100 nM | 200 nM | 300 nM | 400 nM | 500 nM | No Drugs |
|---|---|---|---|---|---|---|
| Frameshift | 8.25 | 8.10 | 7.96 | 8.01 | 8.00 | 8.48 |
| Percentage decrease in frameshift | 2.71 | 4.51 | 6.17 | 5.52 | 5.66 |  |

Frameshift figures, shown in Table 5, were calculated using the formula shown in Example 3 using data from Tables 1, 2, 3 and 4.

The frameshift using the filter-set of 525 excitation and 600LP emission gives a higher frameshift number than the 544 excitation/590 emission filter set due to bleed-through from the EGFP of approximately 2%.

The results show a decrease in frameshift from 8.48% to 8.25% for 100 nM Cycloheximide. This is an absolute change in frameshift efficiency of 0.23% or a decrease by 2.7% from the original 8.48%. The percentage decrease in frameshift for concentration from 100 nM through to 500 nM Cycloheximide can be seen in Table 5. The data demonstrates the utility of the recoding construct and methods of the invention in detecting recoding changes, over a range of concentrations The Z factor, shown in Tables 1 to 4, is an indication of the robustness of an assay and is referred to in Zhang et al—(Dupont: Journal of Biomolecular Screening Vol. 4 No. 2, 1999). The Z factor is calculated according to the formula:

$$Z=1-(3SD \text{ of sample}+3SD \text{ of control})/(\text{mean of sample}-\text{mean of control})$$

A Z factor of between 0.5 and 1.0 (the theoretical maximum) indicates a robust assay. The Z factor decreases in this assay because both cycloheximide and anisomycin are antagonists to −1 frameshifting (see tables 1 through to 4). A Z' factor can be calculated using the control data without addition of any test compounds. A comparison of the Z' and Z factors of the under the same assay conditions reveals the effect of the compounds on the assay. The decreasing Z scores below 0 or above 1.0 arise because the minus 1 frameshift construct signal/number has approached the value of the CV1 control cells. The CV1 control cells are cells which have no reporter genes present, and give a true background.

Example 6

Dual Fluorescent Reporter Recoding Assay at a Range of Anisomycin Concentrations Transfected cells were prepared as described in Example 5, and treated with 0 nM (no drug) 100 nM, 200 nM, 300 nM, 400 nM and 500 nM concentrations of anisomycin.

Incubation, plate reader setting and readings were as described in Example 5. The results are shown in Tables 6 to 10 below:

TABLE 6

Minus 1 Frameshift Construct
DsRed 525 excitation 600LP emission

|  | 100 nM | 200 nM | 300 nM | 400 nM | 500 nM | No Drugs | Controls |
|---|---|---|---|---|---|---|---|
| A | 2891 | 3301 | 2797 | 1673 | 1152 | 2562 | 614 |
| B | 2992 | 3870 | 3185 | 1932 | 1250 | 2491 | 632 |
| C | 3333 | 3495 | 3003 | 1808 | 962 | 2408 | 611 |
| D |  |  |  |  |  |  |  |
| E |  |  |  |  |  |  |  |
| F |  |  |  |  |  |  |  |
| G |  |  |  |  |  |  |  |
| H |  |  |  |  |  |  |  |
| Average | 3072 | 3555 | 2995 | 1804 | 1121 | 2487 | 619 |
| Standard Deviation | 232 | 289 | 194 | 130 | 146 | 77 | 11 |
| Background | 619 | 619 | 619 | 619 | 619 | 619 |  |
| St Dev Background | 11 | 11 | 11 | 11 | 11 | 11 |  |
| Z, Z' factor | 0.70 | 0.69 | 0.74 | 0.64 | 0.06 | 0.86 |  |

TABLE 7

Null 0 Frameshift Construct
DsRed 525 excitation 600LP emission

|   | 100 nM | 200 nM | 300 nM | 400 nM | 500 nM | No Drugs | Controls |
|---|--------|--------|--------|--------|--------|----------|----------|
| A | 50738  | 51831  | 33805  | 16066  | 6401   | 43480    | 614      |
| B | 57204  | 45297  | 38558  | 16946  | 6457   | 43200    | 632      |
| C | 58092  | 52933  | 37960  | 17191  | 8277   | 38238    | 611      |
| D |        |        |        |        |        |          |          |
| E |        |        |        |        |        |          |          |
| F |        |        |        |        |        |          |          |
| G |        |        |        |        |        |          |          |
| H |        |        |        |        |        |          |          |
| Average | 55345 | 50020 | 36774 | 16734 | 7045 | 41639 | 619 |
| Standard Deviation | 4014 | 4127 | 2589 | 592 | 1067 | 2949 | 11 |
| Background | 619 | 619 | 619 | 619 | 619 | 619 | |
| St Dev Background | 11 | 11 | 11 | 11 | 11 | 11 | |
| Z, Z' factor | 0.78 | 0.75 | 0.78 | 0.89 | 0.50 | 0.78 | |

TABLE 8

Minus 1 Frameshift Construct
EGFP 485 excitation 520-P emission

|   | 100 nM | 200 nM | 300 nM | 400 nM | 500 nM | No Drugs | Controls |
|---|--------|--------|--------|--------|--------|----------|----------|
| A | 30289  | 35621  | 29868  | 16958  | 9668   | 25570    | 550      |
| B | 32354  | 41774  | 34077  | 20341  | 10867  | 25136    | 613      |
| C | 33127  | 36190  | 33736  | 18591  | 7594   | 23887    | 554      |
| D |        |        |        |        |        |          |          |
| E |        |        |        |        |        |          |          |
| F |        |        |        |        |        |          |          |
| G |        |        |        |        |        |          |          |
| H |        |        |        |        |        |          |          |
| Average | 31923 | 37862 | 32560 | 18630 | 9376 | 24864 | 572 |
| Standard Deviation | 1467 | 3400 | 2338 | 1692 | 1656 | 874 | 35 |
| Background | 572 | 572 | 572 | 572 | 572 | 572 | |
| St Dev Background | 35 | 35 | 35 | 35 | 35 | 35 | |
| Z, Z' factor | 0.86 | 0.72 | 0.78 | 0.71 | 0.42 | 0.89 | |

TABLE 9

Null 0 Frameshift Construct
EGFP 485 excitation 520-P emission

|   | 100 nM | 200 nM | 300 nM | 400 nM | 500 nM | No Drugs | Controls |
|---|--------|--------|--------|--------|--------|----------|----------|
| A | 51260  | 52705  | 36204  | 17799  | 7345   | 44981    | 550      |
| B | 57780  | 47922  | 40351  | 18806  | 7489   | 45059    | 613      |
| C | 58155  | 54940  | 40233  | 18992  | 9523   | 39660    | 554      |
| D |        |        |        |        |        |          |          |
| E |        |        |        |        |        |          |          |
| F |        |        |        |        |        |          |          |
| G |        |        |        |        |        |          |          |
| H |        |        |        |        |        |          |          |
| Average | 55732 | 51856 | 38929 | 18532 | 8119 | 43233 | 572 |
| Standard Deviation | 3877 | 3585 | 2361 | 642 | 1218 | 3095 | 35 |
| Background | 572 | 572 | 572 | 572 | 572 | 572 | |
| St Dev Background | 35 | 35 | 35 | 35 | 35 | 35 | |
| Z, Z' factor | 0.79 | 0.79 | 0.81 | 0.89 | 0.50 | 0.78 | |

TABLE 10

| Anisomycin Titration | 100 nM | 200 nM | 300 nM | 400 nM | 500 nM | No Drugs |
|----------------------|--------|--------|--------|--------|--------|----------|
| Frameshift | 7.89 | 8.17 | 7.88 | 7.32 | 6.70 | 8.00 |
| Percentage decrease in frameshift | 1.39 | −2.21 | 1.47 | 8.53 | 16.21 | |

For the anisomycin titrations, the frameshift figures, shown in Table 10, were calculated using the formula shown in Example 3 using data from Tables 6, 7, 8 and 9.

The frameshift using the filter-set of 525 excitation and 600LP emission gives a higher frameshift number than the 544 excitation/590 emission filter set due to bleed-through from the EGFP of approximately 2%.

The results show a decrease in frameshift from 7.99% to 7.88% for 100 nM anisomycin. This is an absolute change in frameshift efficiency of 0.11% or a decrease by 1.4% from the original 7.99%. The percentage decrease in frameshift for concentration from 100 nM through to 500 nM Anisomycin can be seen in Table 10. The data demonstrates the utility of the recoding construct and methods of the invention in detecting recoding changes, over a range of concentrations.

Example 7

Stably Transfected Dual Fluorescent Reporter Recoding Assay at a Range of Cycloheximide and Anisomycin Concentrations Flp-In CV1 cells (CV1 cells), as described in Example 2, transfected with the −1 frame construct, and untransfected CV1 cells were grown, harvested, trypsinised, washed and diluted to $1 \times 10^5$ cells/ml all under standard conditions.

Cells were then seeded in 96 well plates under standard conditions. Test compounds were added in triplicate, at a range of concentration between 50 nM and 200 nM as shown in Tables 11, 12, 14 and 15. The plates were then incubated for 120 hours at 37° C.

The cells were washed 3 times with Phosphate Buffered Saline (PBS) to remove any traces of culture medium. 100 ul of Passive Lysis buffer (Promega) was added. The cells were frozen. The frozen cells were then thawed and fluorescence intensity was read in the Tecan Genios Pro plate reader.

Plate reader setting were as follows:
EGFP readings:
Filters 485 excitation, 515 emission
DsRed readings:
Filters 535 excitation, 590 emission Results are shown in Tables 11 to 13 for cyclohexamide and Tables 14 to 16 for anisomysin.

Cycloheximide results for stable Flp-In CV1 cells:

TABLE 11

Minus 1 Frameshift Construct
EGFP 485 excitation 515 emission

| <> | No Drug | 50 nM | 100 nM | 500 nM | 1000 nM | 2000 nM | CV1 control |
|---|---|---|---|---|---|---|---|
| A | 12772 | 11707 | 10613 | 10543 | 7112 | 5888 | 4385 |
| B | 13495 | 10919 | 11799 | 8266 | 7492 | 6236 | 4370 |
| C | 12673 | 11702 | 10128 | 8691 | 6663 | 5804 | 4759 |
| D | 13531 | 11840 | 11245 | 9235 | 7679 | 6403 | 4649 |
| E | 13816 | 9949 | 12146 | 7261 | 6789 | 5989 | 4917 |
| F | 13060 | 11479 | 12598 | 8153 | 8272 | 6924 | 4838 |
| G | 13565 | 10747 | 9610 | 7575 | 6784 | 6065 | 4968 |
| H | 14370 | 12163 | 11957 | 9377 | 7671 | 6974 | 4930 |
| Average | 13410 | 11313 | 11262 | 8638 | 7308 | 6285 | 4727 |
| SD | 561 | 724 | 1054 | 1065 | 565 | 451 | 239 |
| Control | 4727 | 4727 | 4727 | 4727 | 4727 | 4727 | 4727 |
| Z, Z' factor | 0.72 | 0.56 | 0.41 | 0.00 | 0.07 | −0.33 | |

TABLE 12

Minus 1 Frameshift Construct
DsRed 535 excitation 590 emission

| <> | No Drug | 50 nM | 100 nM | 500 nM | 1000 nM | 2000 nM | CV1 control |
|---|---|---|---|---|---|---|---|
| A | 1331 | 1222 | 1096 | 1191 | 771 | 750 | 662 |
| B | 1409 | 1207 | 1222 | 868 | 865 | 674 | 743 |
| C | 1385 | 1265 | 1220 | 962 | 795 | 666 | 752 |
| D | 1395 | 1317 | 1251 | 1016 | 832 | 674 | 746 |
| E | 1444 | 1186 | 1325 | 868 | 808 | 630 | 745 |
| F | 1390 | 1216 | 1343 | 866 | 945 | 799 | 748 |
| G | 1433 | 1200 | 1083 | 864 | 765 | 631 | 758 |
| H | 1428 | 1145 | 1136 | 947 | 760 | 680 | 717 |
| Average | 1402 | 1220 | 1210 | 948 | 818 | 688 | 734 |
| SD | 36 | 52 | 98 | 114 | 63 | 58 | 31 |
| Control | 734 | 734 | 734 | 734 | 734 | 734 | 734 |
| Z, Z' factor | 0.70 | 0.49 | 0.18 | −1.04 | −2.37 | 6.86 | |

TABLE 13

| Cycloheximide Titration in stable cells | 50 nM | 100 nM | 500 nM | 1000 nM | 2000 nM | No Drug |
|---|---|---|---|---|---|---|
| DsRed/EGFP ratio | 7.38 | 7.28 | 5.47 | 3.25 | −2.94 | 7.69 |
| Percentage decrease in ratio | 4.11 | 5.39 | 28.91 | 57.82 | 138.27 | |

Anisomycin results for stably transformed Flp-In cells:

TABLE 14

Minus 1 Frameshift Construct
EGFP 485 excitation 515 emission

| <> | No Drug | 50 nM | 100 nM | 500 nM | 1000 nM | 2000 nM | CV1 control |
|---|---|---|---|---|---|---|---|
| A | 12772 | 12317 | 11710 | 8846 | 8036 | 7092 | 4385 |
| B | 13495 | 12159 | 11538 | 9931 | 7650 | 7895 | 4370 |
| C | 12673 | 11498 | 11913 | 8485 | 8342 | 7376 | 4759 |
| D | 13531 | 12489 | 12822 | 8699 | 8249 | 8610 | 4649 |
| E | 13816 | 13573 | 14270 | 9246 | 8594 | 8013 | 4917 |
| F | 13060 | 12407 | 12426 | 9634 | 9132 | 8152 | 4838 |
| G | 13565 | 12615 | 11150 | 8001 | 8613 | 7085 | 4968 |
| H | 14370 | 13644 | 11672 | 8971 | 8469 | 7228 | 4930 |
| Average | 13410 | 12588 | 12188 | 8977 | 8386 | 7681 | 4727 |
| SD | 561 | 715 | 990 | 621 | 438 | 566 | 239 |
| Control | 4727 | 4727 | 4727 | 4727 | 4727 | 4727 | 4727 |
| Z, Z' factor | | 0.72 | 0.64 | 0.51 | 0.39 | 0.44 | 0.18 |

TABLE 15

Minus 1 Frameshift Construct
DsRed 535 excitation 590 emission

| <> | No Drug | 50 nM | 100 nM | 500 nM | 1000 nM | 2000 nM | CV1 control |
|---|---|---|---|---|---|---|---|
| A | 1331 | 1321 | 1221 | 799 | 692 | 618 | 662 |
| B | 1409 | 1376 | 1282 | 880 | 651 | 637 | 743 |
| C | 1385 | 1294 | 1311 | 762 | 720 | 641 | 752 |
| D | 1395 | 1372 | 1374 | 809 | 708 | 699 | 746 |
| E | 1444 | 1438 | 1487 | 834 | 732 | 684 | 745 |
| F | 1390 | 1318 | 1298 | 827 | 754 | 656 | 748 |
| G | 1433 | 1339 | 1248 | 738 | 729 | 609 | 758 |
| H | 1428 | 1322 | 1188 | 710 | 648 | 587 | 717 |
| Average | 1402 | 1348 | 1301 | 795 | 704 | 641 | 734 |
| SD | 36 | 46 | 94 | 55 | 38 | 38 | 31 |
| Control | 734 | 734 | 734 | 734 | 734 | 734 | 734 |
| Z, Z' factor | | 0.70 | 0.62 | 0.33 | −3.27 | 8.06 | 3.24 |

TABLE 16

| Anisomycin Titration in stable cells | 50 nM | 100 nM | 500 nM | 1000 nM | 2000 nM | No Drug |
|---|---|---|---|---|---|---|
| DsRed/EGFP ratio | 7.81 | 7.60 | 1.44 | −0.81 | −3.13 | 7.69 |
| Percentage decrease in ratio | −1.47 | 1.17 | 81.34 | 110.53 | 140.70 | |

As a Null 0 frameshift construct was not used in this experiment ratios of the DsRed to EGFP signal were calculated to take into account the decrease in the EGFP signal with increasing drug concentrations.

The calculation was similar to example 3, with the counts averaged, the control cell counts removed before working out the ratio of the DsRed signal to the EGFP signal. Normalisation using a Null 0 frame construct could not be performed, with the results below being expressed as a percentage. The calculation was a follows:

[[DsRed signal: HIV-1 frameshift construct]/[EGFP signal: HIV-1 frameshift construct]]

The % "decrease in ratio" data for each cyclohexamide concentration, shown in Table 13, indicates a dose responsive effect in the range between 50 nM and 2000 nM cyclohexamide. This data demonstrates the utility of the recoding construct and methods of the invention in detecting recoding changes over a range of concentrations.

The % "decrease in ratio" data for each anisomycin concentration, shown in Table 16, indicates a dose responsive effect in the range between 50 nM and 2000 nM anisomycin. This data further demonstrates the utility of the recoding construct and methods of the invention in detecting recoding changes over a range of concentrations.

The use of the Z factor allows for qualitative interpretation of any compound/drug trials. A reduction of the Z factor to zero indicates a yes/no assay, and a number less than zero means that screening is essentially impossible. The compounds tested in the assays did decrease the Z factor with increasing drug/compound concentrations, with compound concentrations over 500 nM having a strong effect on the Z factor in the 120 hour assay that used stably transfected cells.

The above example illustrates practice of the invention. It will be appreciated by those skilled in the art that numerous variations and modifications may be made without departing from the spirit and scope of the invention.

The invention claimed is:

1. A translational recoding reporter construct comprising:
   a) a first fluorescent protein coding sequence;
   b) a second fluorescent protein coding sequence encoding a fluorescent protein different from the first fluorescent protein;
   c) a linker sequence interposed between the first and second fluorescent protein coding sequences; and
   d) a recoding signal sequence interposed between the first fluorescent protein coding sequence and the second fluorescent protein coding sequence, wherein said recoding signal sequence comprises the sequence of SEQ ID NO:8;
   wherein the first fluorescent protein coding sequence and the second fluorescent protein coding sequence are out-of-frame with respect to each other but are able to be co-expressed as a single fusion polypeptide upon recoding, and wherein the linker sequence encodes a polypeptide capable of physically separating the co-expressed fluorescent proteins, and wherein said linker sequence encodes a polypeptide comprising the sequence of SEQ ID NO:1, resulting in increased fluorescence output from each protein.

2. The translational recoding reporter construct of claim 1 wherein the polypeptide encoded by the linker sequence is capable of reducing fluorescence resonance energy transfer (FRET) between the co-expressed fluorescent proteins.

3. The translational recoding reporter construct of claim 1 in which the linker comprises the sequence of SEQ ID NO:2.

4. The translational recoding reporter construct of claim 1 in which the fluorescent proteins are a red fluorescent protein and a green fluorescent protein.

5. The translational recoding reporter construct of claim 1 in which the recoding signal sequence is interposed between the first fluorescent protein coding sequence and the linker sequence.

6. An isolated host cell comprising a translational recoding reporter construct of claim 1.

\* \* \* \* \*

UNITED STATES PATENT AND TRADEMARK OFFICE
CERTIFICATE OF CORRECTION

PATENT NO. : 8,389,236 B2
APPLICATION NO. : 12/065258
DATED : March 5, 2013
INVENTOR(S) : Cardno et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1379 days.

Signed and Sealed this
First Day of September, 2015

Michelle K. Lee
*Director of the United States Patent and Trademark Office*

SEQUENCE LISTING

<160> NUMBER OF SEQ ID NOS: 14

<210> SEQ ID NO 1
<211> LENGTH: 12
<212> TYPE: PRT
<213> ORGANISM: Artificial
<220> FEATURE:
<223> OTHER INFORMATION: Synthetic construct

<400> SEQUENCE: 1

Ala Glu Ala Ala Ala Lys Glu Ala Ala Ala Lys Ala
1               5                   10

<210> SEQ ID NO 2
<211> LENGTH: 36
<212> TYPE: DNA
<213> ORGANISM: Artificial
<220> FEATURE:
<223> OTHER INFORMATION: Synthetic construct

<400> SEQUENCE: 2
gccgaagcag ccgccaaaga agcagccgcc aaagct                                 36

<210> SEQ ID NO 3
<211> LENGTH: 61
<212> TYPE: DNA
<213> ORGANISM: Artificial
<220> FEATURE:
<223> OTHER INFORMATION: Synthetic construct

<400> SEQUENCE: 3
ggacaggcta atttttagg gaagatctgg ccttcctaca agggaaggcc agggaattt          60 c                                                                       61

<210> SEQ ID NO 4
<211> LENGTH: 40
<212> TYPE: DNA
<213> ORGANISM: Artificial
<220> FEATURE:
<223> OTHER INFORMATION: Synthetic construct useful as a primer

<400> SEQUENCE: 4
gatccgaagc ttgccaccat ggtgagcaag ggcgaggagc                             40

<210> SEQ ID NO 5
<211> LENGTH: 30
<212> TYPE: DNA
<213> ORGANISM: Artificial
<220> FEATURE:
<223> OTHER INFORMATION: Synthetic construct useful as a primer

<400> SEQUENCE: 5
gcggccgaat tccttgtaca gctcgtccat                                        30

<210> SEQ ID NO 6
<211> LENGTH: 35
<212> TYPE: DNA
<213> ORGANISM: Artificial
<220> FEATURE:
<223> OTHER INFORMATION: Synthetic construct useful as a primer

<400> SEQUENCE: 6
gtcgccaccg gatcctcctc cgaggacgtc atcaa                                  35

```
<210> SEQ ID NO 7
<211> LENGTH: 24
<212> TYPE: DNA
<213> ORGANISM: Artificial
<220> FEATURE:
<223> OTHER INFORMATION: Synthetic construct useful as a primer

<400> SEQUENCE: 7
ctagagtcgc ggccgctaca ggaa                                           24

<210> SEQ ID NO 8
<211> LENGTH: 78
<212> TYPE: DNA
<213> ORGANISM: Artificial
<220> FEATURE:
<223> OTHER INFORMATION: Synthetic construct

<400> SEQUENCE: 8
aattcggaca ggctaatttt ttagggaaga tctggccttc ctacaaggga aggccaggga   60
attttcttta aacgccgc                                                  78

<210> SEQ ID NO 9
<211> LENGTH: 72
<212> TYPE: DNA
<213> ORGANISM: Artificial
<220> FEATURE:
<223> OTHER INFORMATION: Synthetic construct

<400> SEQUENCE: 9
ggcgtttaaa gaaaattccc tggccttccc ttgtaggaag gccagatctt ccctaaaaaa   60
ttagcctgtc cg                                                        72

<210> SEQ ID NO 10
<211> LENGTH: 79
<212> TYPE: DNA
<213> ORGANISM: Artificial
<220> FEATURE:
<223> OTHER INFORMATION: Synthetic construct

<400> SEQUENCE: 10
atttcggaca ggctaatttc ctaagggaag atctggcctt cctacaaggg aaggccaggg   60
aattttcctt aaacgccgc                                                 79

<210> SEQ ID NO 11
<211> LENGTH: 73
<212> TYPE: DNA
<213> ORGANISM: Artificial
<220> FEATURE:
<223> OTHER INFORMATION: Synthetic construct

<400> SEQUENCE: 11
ggcgtttaaa gaaaattccc tggccttccc ttgtaggaag gccagatctt cccttaggaa   60
aatagcctgt ccg                                                       73

<210> SEQ ID NO 12
<211> LENGTH: 47
<212> TYPE: DNA
<213> ORGANISM: Artificial
<220> FEATURE:
<223> OTHER INFORMATION: Synthetic construct

<400> SEQUENCE: 12
gggcccggcc gaagcagccg ccaaagaagc agccgccaaa gctaccg                  47
```

```
<210> SEQ ID NO 13
<211> LENGTH: 53
<212> TYPE: DNA
<213> ORGANISM: Artificial
<220> FEATURE:
<223> OTHER INFORMATION: Synthetic construct

<400> SEQUENCE: 13
gatccggtac cggctttggc ggctgcttct ttggcggctt cggccgggcc cgc          53

<210> SEQ ID NO 14
<211> LENGTH: 81
<212> TYPE: DNA
<213> ORGANISM: Artificial
<220> FEATURE:
<223> OTHER INFORMATION: Synthetic construct

<400> SEQUENCE: 14
gaattcggac aggctaattt tttagggaag atctggcctt cctacaaggg aaggccaggg   60
aattttcttt aaacgccgcg g                                             81
```